United States Patent
Bozdog et al.

(10) Patent No.: US 10,534,275 B2
(45) Date of Patent: Jan. 14, 2020

(54) METHOD FOR USE IN PROCESS CONTROL OF MANUFACTURE OF PATTERNED SAMPLE

(71) Applicant: NOVA MEASURING INSTRUMENTS LTD., Rehovot (IL)

(72) Inventors: Cornel Bozdog, San Jose, CA (US); Aron Cepler, Albany, NY (US); Paul Isbester, Castleton, NY (US)

(73) Assignee: NOVA MEASURING INSTRUMENTS LTD., Rehovot (IL)

( * ) Notice: Subject to any disclaimer, the term of this patent is extended or adjusted under 35 U.S.C. 154(b) by 109 days.

(21) Appl. No.: 15/739,250

(22) PCT Filed: Jun. 22, 2016

(86) PCT No.: PCT/IL2016/050667
§ 371 (c)(1),
(2) Date: Dec. 22, 2017

(87) PCT Pub. No.: WO2016/207891
PCT Pub. Date: Dec. 29, 2016

(65) Prior Publication Data
US 2018/0196356 A1  Jul. 12, 2018

Related U.S. Application Data

(60) Provisional application No. 62/182,681, filed on Jun. 22, 2015.

(51) Int. Cl.
*G03F 7/20* (2006.01)
*G01N 21/956* (2006.01)
(Continued)

(52) U.S. Cl.
CPC ...... *G03F 7/70633* (2013.01); *G03F 7/70466* (2013.01); *G03F 7/70625* (2013.01);
(Continued)

(58) Field of Classification Search
CPC ............ G03F 7/70683; G03F 7/70633; G03F 7/70466; G03F 7/70525; G03F 7/70625;
(Continued)

(56) References Cited

U.S. PATENT DOCUMENTS 6,271,047 B1 * 8/2001 Ushio .................. B24B 37/013
257/E21.528
8,283,111 B2 10/2012 Fonseca et al.
(Continued)

OTHER PUBLICATIONS

Chao, et al., abstract only, Advanced in-line metrology strategy for self-aligned quadruple patterning, Proc. SPIE 9778, Metrology, Inspection, and Process Control for Microlithography, Mar. 30, 2016, pp. 977813-1-12.

*Primary Examiner* — Ali Bayat
(74) *Attorney, Agent, or Firm* — Alphapatent Associates, Ltd; Daniel J. Swirsky

(57) ABSTRACT

A method and system are presented for use in controlling a multiple patterning process of n patterning stages subsequently applied to a sample to produce a target pattern thereon. The method comprises: providing intermediate measured data indicative of an optical response of the sample after being patterned by m-th patterning stage, $1 \leq m < n$; processing said intermediate measured data, determining at least a location parameter of a predetermined feature of the pattern, and generating measured data indicative of said at least one selected parameter; utilizing said at least location parameter of the predetermined feature for optimizing a data interpretation model for interpretation of measured data indicative of an optical response from the sample being patterned by k-th subsequent patterning stage, $m < k \leq n$.

13 Claims, 9 Drawing Sheets

(51) Int. Cl.
  *G01N 21/21* (2006.01)
  *H01L 21/66* (2006.01)
  *H01L 21/8234* (2006.01)

(52) U.S. Cl.
  CPC ..... *G01N 21/956* (2013.01); *G01N 2021/213* (2013.01); *H01L 21/823431* (2013.01); *H01L 22/12* (2013.01); *H01L 22/20* (2013.01)

(58) Field of Classification Search
  CPC .......... G03F 7/70616; G03F 1/24; G03F 1/76; G03F 1/80; G03F 17/5081; G03F 2217/12; G01N 21/956; G01N 2021/213; H01L 21/823431; H01L 21/845; H01L 22/12; H01L 22/20
  USPC ........................................................ 382/145
  See application file for complete search history.

(56) References Cited

U.S. PATENT DOCUMENTS

| | | |
|---|---|---|
| 8,531,678 B2 | 9/2013 | Finarov et al. |
| 2002/0031249 A1* | 3/2002 | Komuro ............. G01N 21/9501 382/149 |
| 2004/0248043 A1* | 12/2004 | Shiraishi ................... G03F 1/30 430/311 |
| 2005/0010890 A1* | 1/2005 | Nehmadi .................. G03F 1/36 700/121 |
| 2006/0134529 A1* | 6/2006 | Hansen ............... G03F 7/70425 430/5 |
| 2006/0256322 A1* | 11/2006 | Bowes .................... G03F 7/706 356/124 |
| 2007/0229854 A1 | 10/2007 | Wu et al. |
| 2010/0017005 A1 | 1/2010 | Adel et al. |
| 2010/0161099 A1 | 6/2010 | Mos et al. |
| 2011/0026017 A1* | 2/2011 | Hayano ............ G01N 21/95692 356/237.5 |
| 2012/0076393 A1 | 3/2012 | Ivanchenko et al. |
| 2012/0133938 A1* | 5/2012 | Deckers ............... G03F 7/70625 356/388 |
| 2014/0036243 A1 | 2/2014 | Beyer et al. |
| 2016/0109230 A1 | 4/2016 | Pandev et al. |

* cited by examiner

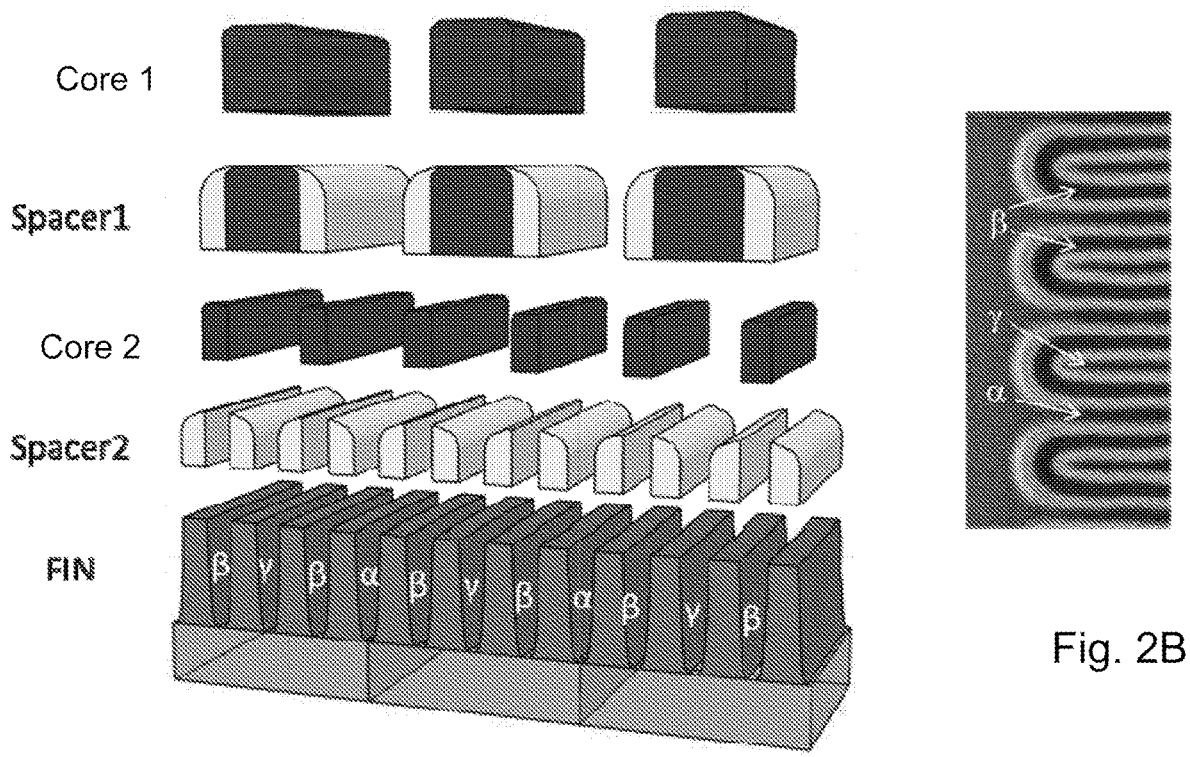
Fig. 2A
Fig. 2B
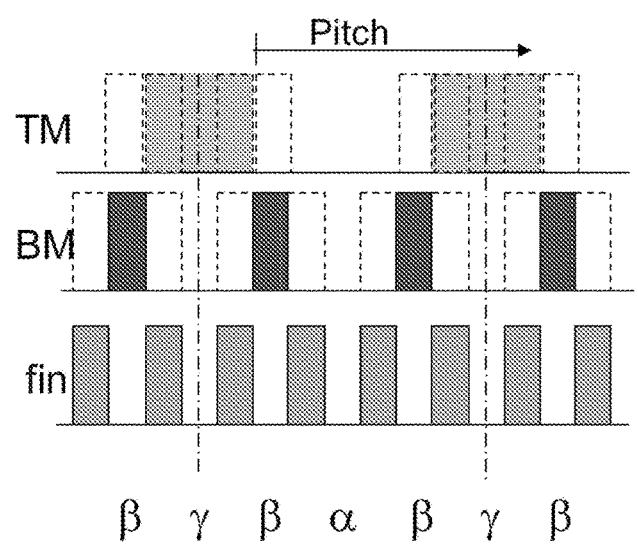
Fig. 2C

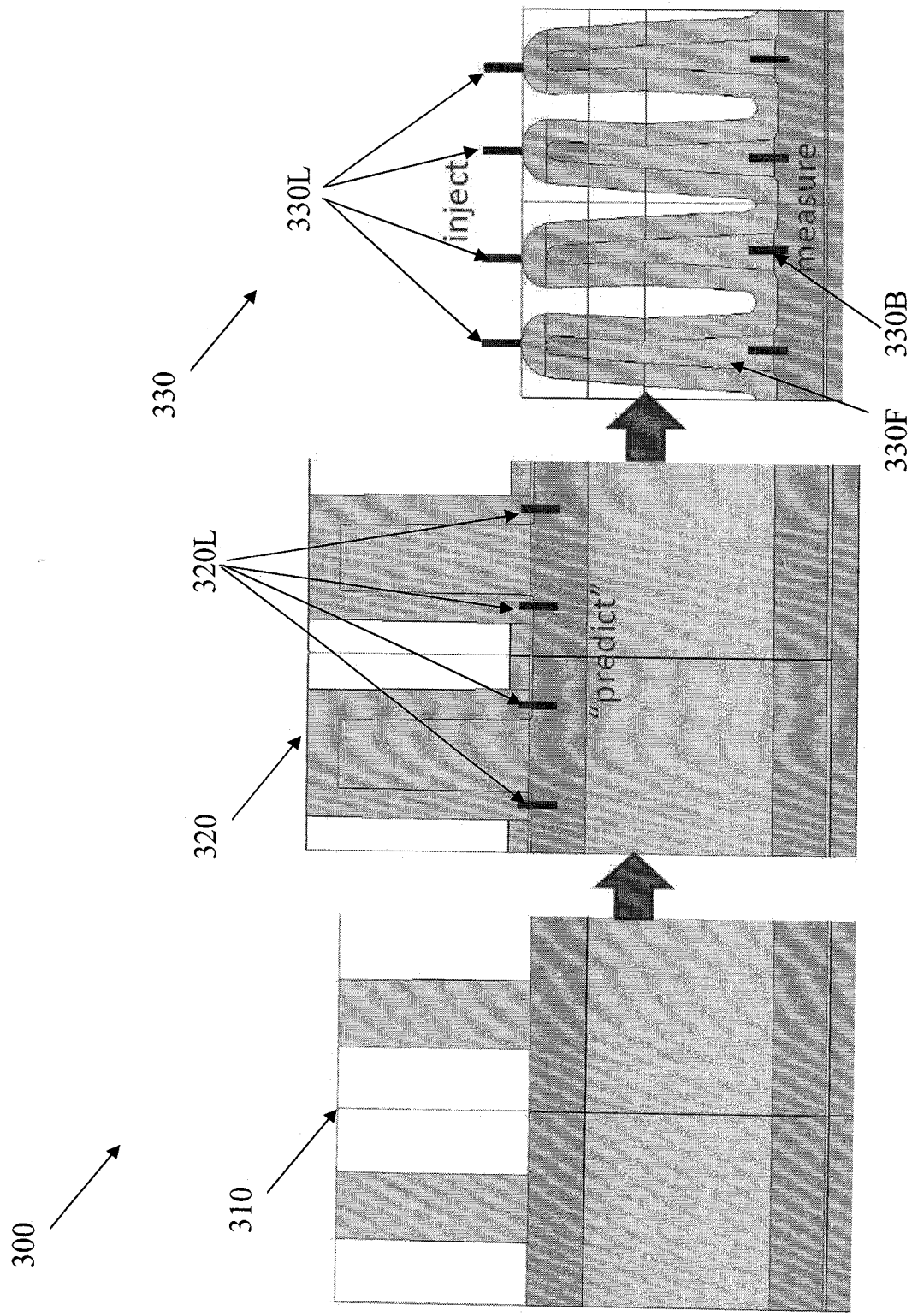

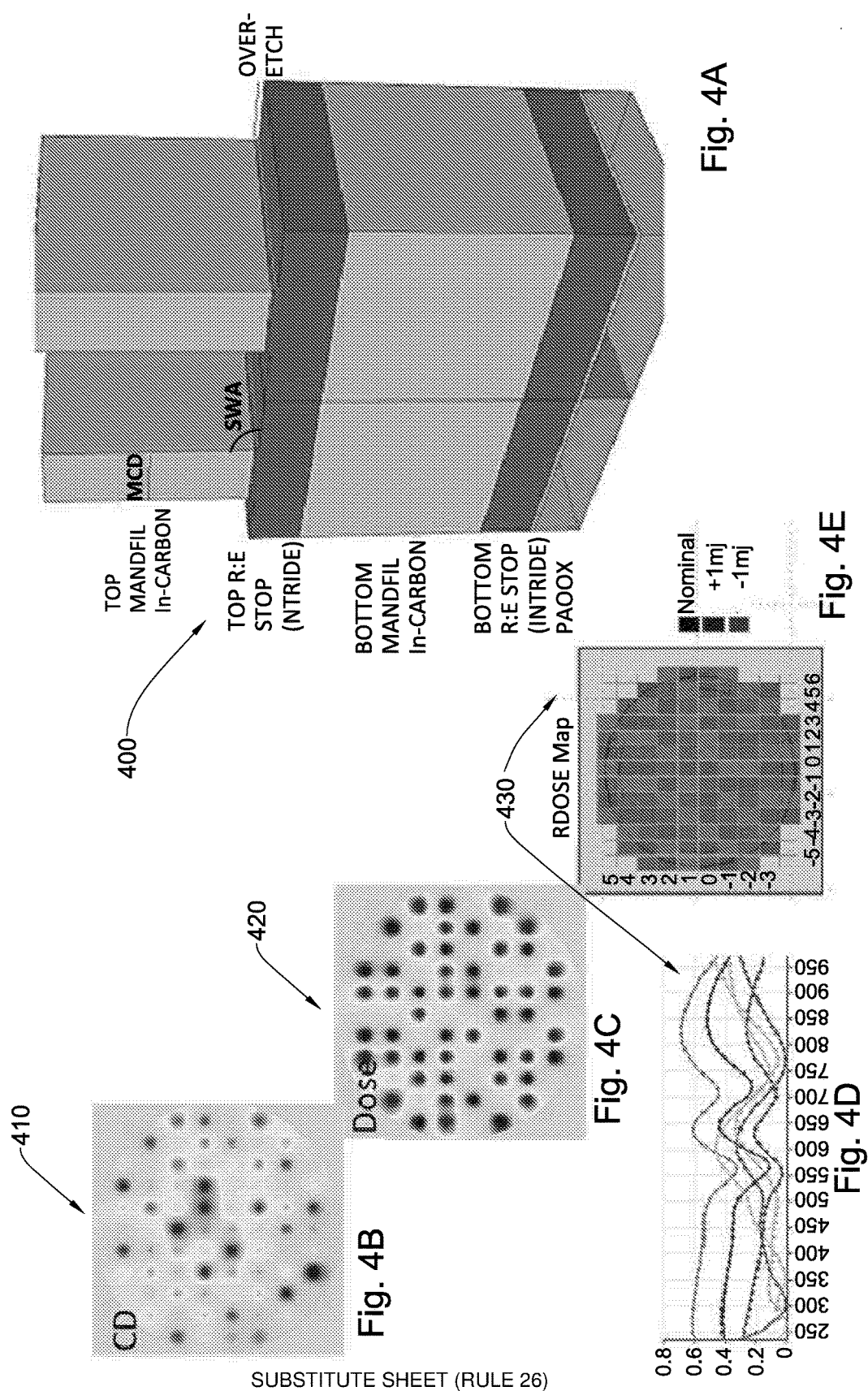

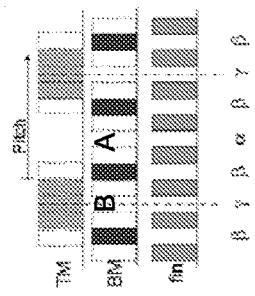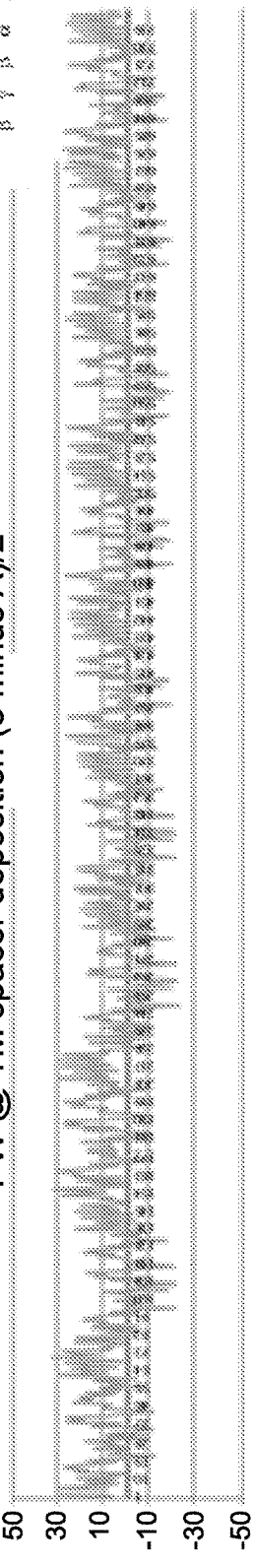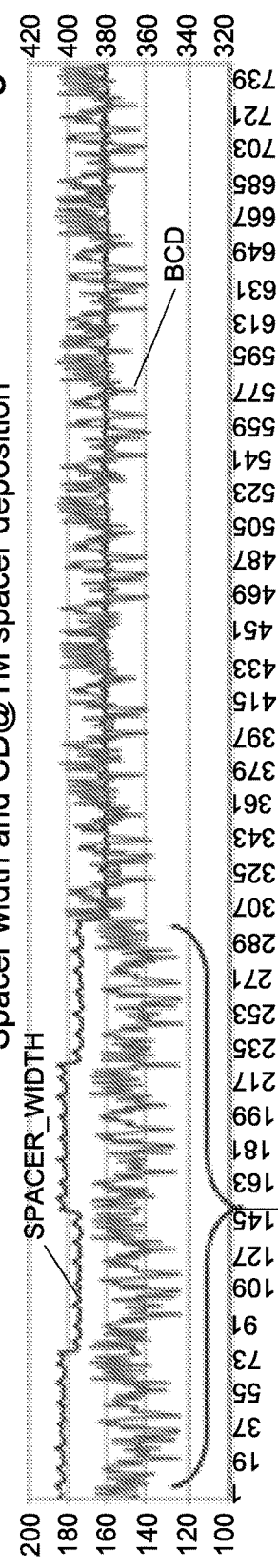

METHOD FOR USE IN PROCESS CONTROL OF MANUFACTURE OF PATTERNED SAMPLE

TECHNOLOGICAL FIELD

The present invention is generally in the field of process control techniques for controlling the process of manufacture of patterned samples, and relates to a metrology method and system for measuring in patterned samples being manufactured by multiple patterning process.

BACKGROUND

Metrology processes are used for monitoring and controlling various steps of a semiconductor manufacturing process by measuring parameters of a wafer, such as line width, thickness, angle, etc. As a demand for shrinking semiconductor devices continues to increase, multiple patterning technologies are used for manufacturing integrated circuits (ICs) to enhance the pattern feature density.

Integrated circuit (IC) chips are formed on semiconductor wafers at increasingly smaller scale. In current technology nodes, transistor devices are constructed as three-dimensional (3D) fin field effect transistor (FINFET) structures (i.e. Field Effect transistor in which the conducting channel is wrapped by a thin silicon "fin", which forms the body of the device). The fins of the FINFETS are expected to be constructed as repeating, equally spaced, vertical structures on the wafer. Equally spaced gates are formed as repeating vertical structures that overlay the fins in an orthogonal direction.

A simplest example of the multiple patterning techniques is a double patterning, which allows the patterning of smaller features at a smaller pitch than what is currently possible with standard lithographic techniques. To this end, standard lithographic pattern-and-etch techniques can be applied to the same substrate twice, thereby forming larger patterns spaced closely together to achieve a smaller feature size than would be possible by single exposure. During double patterning, a layer of radiation-sensitive material on the substrate is exposed to a first pattern, which is developed and transferred to an underlying layer using an etching process, and then these standard lithography steps are repeated for a second pattern, while shifting the second pattern relative to the first pattern.

Another approach to double the resolution of a lithographic pattern is to utilize a dual-tone development technique, wherein a layer of radiation-sensitive material on the substrate is exposed to a pattern of radiation, and then a double pattern is developed into the layer of radiation-sensitive material. Such dual-tone development techniques are described for example in U.S. Pat. No. 8,283,111.

In general, multiple patterning lithography process, which may be double, triple, quadruple, etc. patterning process, requires multiple photolithographic masks for the printing of a single layer on a wafer. Therefore, a multiple patterning lithography process adds a new contribution to the overlay error, which is associated with a placement error of two or several masks used to form the pattern for a single layer on the wafer. An overlay error in a pattern generated with a self-aligned double patterning technique is known as "pitch walking" effect.

For example, US patent publication No. 2014/036243 describes a method for correcting at least one error on wafers processed by at least one of at least two photolithographic masks used in a multiple patterning lithography process. This method includes measuring the at least one error at a wafer processing site, and modifying the at least one photolithographic mask by introducing at least one arrangement of local persistent modifications in the photolithographic mask. This technique suggests using a so-called hard material photo resist of a sacrificial layer on top of a layer to be etched in a self-aligned double patterning process, and introducing an arrangement of local persistent modifications or the pixels in the sacrificial layer to avoid a variation of the lines during the etching of the layer underneath the sacrificial layer, to thereby prevent "pitch walking" effects during the etching step. Pitch walking effect is associated with a CD error in the sacrificial layer that causes overlay-like error in the final pattern. A challenge in constructing the repeating structures such as fins and gates at these advanced technology nodes is that variability in pitch spacing between the structures and pitch walking can occur during the formation of the structures using current sidewall image transfer (SIT) photolithography techniques.

As described above, multiple patterning applications, such as spacer self-aligned multiple patterning (pitch splitting) create arrays of lines/spaces with overlay appearance as a difference between lines and spaces that are located at the same level (same material and same layer). Pitch splitting is done to overcome limitations of the illumination wavelength and numerical apertures used at the exposure stage.

Usually, measurements of the multiple patterning applications are performed on real structures, with real design rules periods/CDs. This makes the "standard" overlay (OL) measurement techniques less applicable for monitoring and controlling the multiple patterning processes. Both Image Based Overlay (IBO) and Diffraction Based Overlay (DBO) have difficulties for measuring structures with minimal periods and CDs and may require larger features. For majority of multiple patterning schemes, especially for such applications as Spacer Self-Aligned Double Patterning (SADP), it is difficult to create features that are much larger than design rules. In addition, modern and promising overlay measurement techniques, such as first order DBO and Muller Matrix based DBO schemes, while being considered as capable of perfectly measuring regular overlay, cannot show benefits in measurements of such an effect as "pitch walking" due to the lack of asymmetry. As indicated above, the pitch walking effect is associated with an overlay error in a pattern generated with a self-aligned multiple patterning technique.

GENERAL DESCRIPTION

As described above, self-aligned multiple patterning technique involves successive etching and spacer deposition steps which induce pitch walking. Pitch walking causes problem for later processes which work on the assumption of consistent spacing between fins, which impacts on yield and device performance. Moreover, after post fin formation, pitch walking is very difficult to measure by using in-line Scatterometry based optical critical dimensions (OCD) techniques. Direct measurement of pitch walking (or differences between two adjustment spaces) is problematic for the standard OCD techniques that are less sensitive to the CD difference, especially when differences are small. Pitch walking (or differences in CDs of two or more spaces) is usually small, and its effect on the optical response of the sample is weak, and it is thus difficult to measure pitch walking parameter compared to the CD of the lines.

As indicated above, metrology methods are used for determining parameters of a sample (geometric parameters and materials characteristics of the pattern in the sample), while the accuracy of measuring these parameters is directly determined by the effect of these parameters on measured optical response (e.g. spectral response). It is hence of great interest to be able to increase the sensitivity of measurements to parameters of interest, possibly at the price of the sensitivity to those parameters which are not of interest or of less interest for the monitoring process. Those parameters for which small changes in value have a strong effect on the measured reflection from the sample (optical response) are commonly termed 'strong', and can be monitored with great accuracy. Conversely, 'weak' parameters are those which have a small effect on the measured reflection (optical response), and their accurate metrology is highly challenging. It should be noted that the terms "reflected" and "reflection" as used in the present application should interpreted broadly as "optical response to illumination", and include specular and non-specular reflection such as scattering.

The present invention provides a novel approach for controlling a multiple patterning process of a sample. The technique of the invention can be applied to a real pattern being created or to a test structure being created (patterned) concurrently with the real pattern. The "test structure" may for example be located in a margin region of a sample outside a real pattern region.

According to the invention, a measurement session (one or more measurements) is performed on a sample at or after a certain patterning stage prior to the last patterning stage. Such prior-to-final patterning stage is at time referred to as "intermediate" patterning stage. However, it should be understood that in case of double patterning technique, such intermediate patterning stage is actually the first stage. So, the term "intermediate" should be interpreted broadly. More specifically, considering n patterning stages (n≥2), an intermediate patterning stage is the m-th stage, where m≥1<n. This "intermediate" measurement session is thus applied to the sample at or after m-th patterning stage being aimed at measuring one or more predetermined parameters of a certain pattern feature, for optimizing interpretation of measured data obtained on the sample at one or more successive patterning stages, e.g. on the final pattern resulting from the n-th patterning stage, i.e. for optimizing the data interpretation model for measurements on the k-th patterning stage where k>m, e.g. k=n.

It should be noted that the feature whose parameter(s) is/are selected for measurement at or after m-th patterning stage for controlling parameters of the pattern of k-th patterning stage may not be present in the pattern created at the k-th patterning stage, but the selected feature parameter of the m-th patterning stage is that affecting the pattern of the k-th patterning stage, and therefore affecting optical response of the k-th pattern.

It should also be noted that the technique of the present invention does not require modification of existing scatterometry measurement systems and various measurement hardware can be utilized. Raw measurement data for "pitch walking" can be obtained by using oblique or normal-incidence reflectometry, ellipsometry, angle-resolved and phase-based systems or combinations thereof. Broadband or predetermined wavelength(s), various polarizations, various angles of incidence and azimuth could be used. Bright, dark and "grey-field" configurations also could be used.

According to one broad aspect of the invention, there is provided a method for use in controlling a multiple patterning process of n patterning stages subsequently applied to a sample to produce a target pattern thereon. The method comprises: providing intermediate measured data indicative of an optical response of the sample after being patterned by m-th patterning stage, 1≤m<n; processing said intermediate measured data, determining at least a location parameter of a predetermined feature of the pattern, and generating measured data indicative of said at least location parameter of the predetermined feature; utilizing said at least one location parameter of the predetermined feature for optimizing a data interpretation model for interpretation of measured data indicative of an optical response from the sample after being patterned by k-th subsequent patterning stage, m<k≤n.

The intermediate measured data may be processed using a data interpretation model for determining the at least one parameters of the sample.

The selected parameter(s) include at least the location of the predetermined feature. For example, this may be the location of a center of a spacer region between neighboring features (lines) of the pattern.

The sample may include a core patterned structure and the at least one selected parameter may include at least one of α, β and γ trenches. As known, and will also be described further below, α, β and γ are three population of trenches appearing at the end of the Self-Aligned Quadruple Patterning (SAQP) process, and the maximum difference between these three populations is defined as pitch walk. At various steps of SAQP, process errors and the non-uniformities across the wafer for parameters like CD and profile, contribute to final non-zero pitch walk. The accurate control of these parameters is extremely important for both process development and high volume production.

The processing of the measured data may further comprise predicting a pitch profile of a pattern in the core patterned structure, depositing a spacer having geometry parameters of a certain profile according to the predicted pitch profile on top of the core patterned structure; etching a spacer according to said profile; measuring at least one pitch walk parameter of the pattern at a bottom of the core patterned structure, and comparing a predicted profile of the pitch with the measured pitch walk parameter. The predicting of the pitch value may include calculating at least one of relative or absolute locations of the center of spacers defined on both sides of the core patterned structure and relative or absolute locations of inner edges of spacers defined on both sides of the core patterned structure. The pitch walk parameter(s) may include individual depth of RIE for each of α, β and γ trenches.

The technique of the invention may utilize measurements on a test structure having a periodic patterned structure comprising a series of sets of patterned features. A core mask may be applied to the test structure to create a first pattern defining the core patterned structure. The optical measurements are applied to the test structure and to detect the optical responses of the periodic structure, and processing of the measured data provides for determining a differential optical response and identifying the pitch of the pattern.

According to another aspect of the invention, it provides a system for use in controlling a multiple patterning process of n patterning stages subsequently applied to a sample to produce a target pattern thereon. The system comprises a control unit, which comprises: data input utility for receiving intermediate measured data corresponding to optical response from the sample after being patterned by m-th patterning stage, 1≤m<n; a processor utility comprising an identification module adapted for processing the intermediate measured data, determining at least a location parameter of a predetermined feature of the pattern, and an interpretation module configured for utilizing said at least location parameter for optimizing a data interpretation model and defining an optimal optical model for interpretation of measured data indicative of an optical response of the sample after being patterned by subsequent k-th patterning stage, m<k≤n.

It should be understood that the parameters of the model include at least some (or even all) of the parameters of the patterned structure. These may include at least some of the following: CD, top CD, bottom CD, sidewall angle, spacer widths, spacer pull-down, epitaxial proximity, footing/undercut overfill/underfill parameters, rounding, etc. Usually, not all of the model parameters, are parameters of interest (i.e. target parameters).

The inventors of the present invention have showed that this scatterometry based solution produces best results to measure pitch walk related parameters ($\alpha$, $\beta$, $\gamma$) as compared to the different approaches described above. This simple and accurate solution is suitable for inline control for Advanced Process Control (APC) for Spacer Assisted Quadra Patterning (SAQP) process in High Volume Manufacturing (HVM).

In some embodiments, the technique of the invention utilizes external injection of measurements for determination of one or more pattern parameters (e.g. pitch parameters) of the structure. The pitch parameters transferred are physical parameters common between steps (thicknesses, CDs, Side Wall Angle (SWA)s). These feature values could be injected into the model ("constant" profile parameters) and/or used as a starting point for interpretation. Measurements can be done on all relevant sites on the wafer, and only relevant information will be injected.

In some embodiments, the parameter(s) selected for intermediate measurements include a location of a certain feature (for example, the relative or absolute locations of center of spacers on both sides of the mandrel/core, or those of inner edges of spacers on both sides of the mandrel/core), and the measured data is transferred to subsequent steps. The transferred location data can be then be used to fix the location of another feature at the subsequent step (using an adjustment function if needed), and float other aspects of the subsequent step. The complete optical model includes most (or even all) parameters describing the structure which are floating parameters. The configuration (modification) of the complete optical model is created by fixing the value of one or more of the model parameters.

BRIEF DESCRIPTION OF THE DRAWINGS

In order to better understand the subject matter that is disclosed herein and to exemplify how it may be carried out in practice, embodiments will now be described, by way of non-limiting examples only, with reference to the accompanying drawings, in which:

FIG. 2A illustrates an example of a sample being patterned by m patterning stages;

FIG. 2B illustrates a SEM picture of the sample of FIG. 2A;

FIG. 2C illustrates different pitch walking parameters $\alpha$, $\beta$ and $\gamma$ with respect to the top mandrel/core, the bottom mandrel and the fin structure;

FIGS. 3A-3E illustrate the different steps of the method according to some embodiments of the present invention; and FIGS. 4A-4K illustrating the different steps of the method according to some embodiments of the present invention.

DETAILED DESCRIPTION OF EMBODIMENTS

Figure 1:
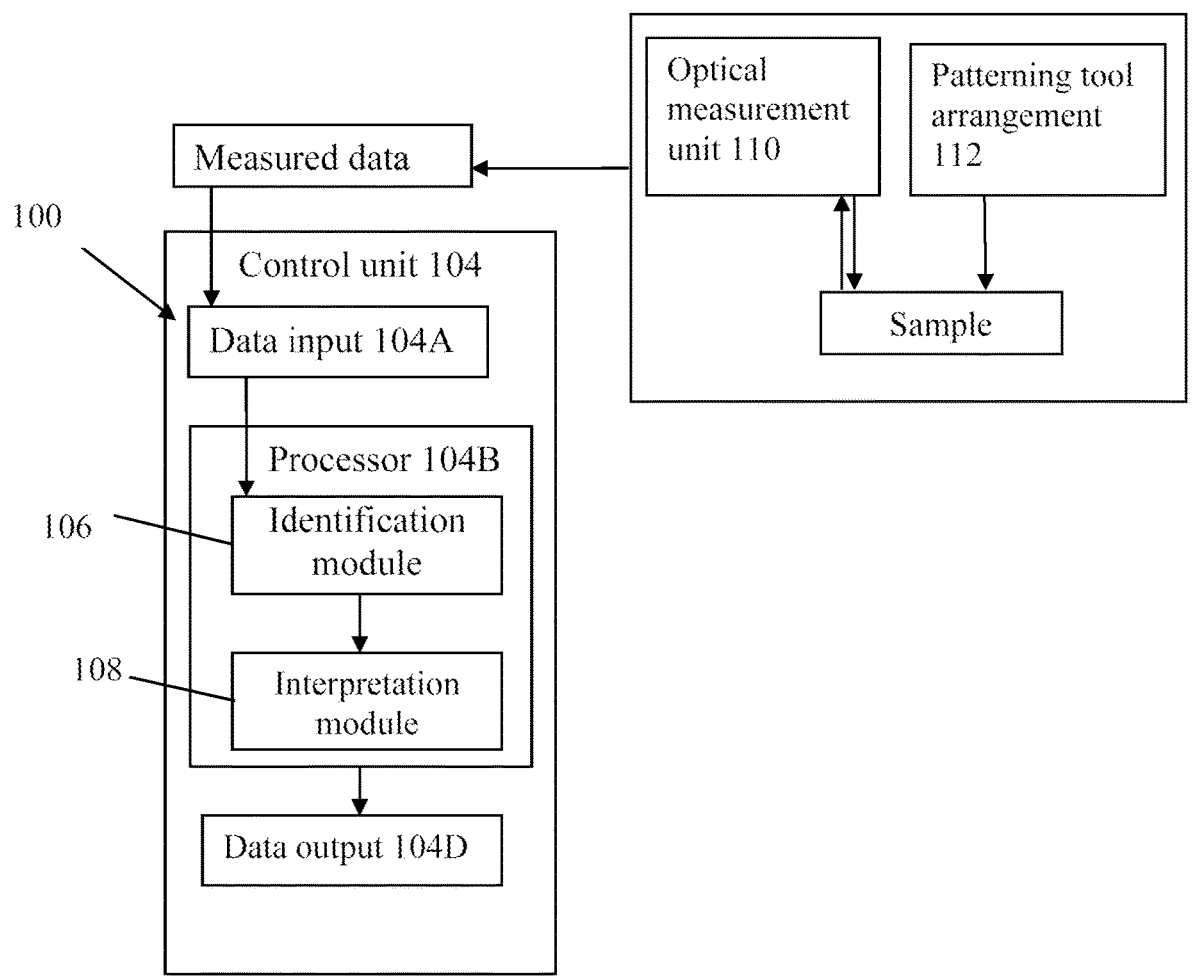
FIG. 1 is a block diagram of the system of the present invention.
Figure 3D:
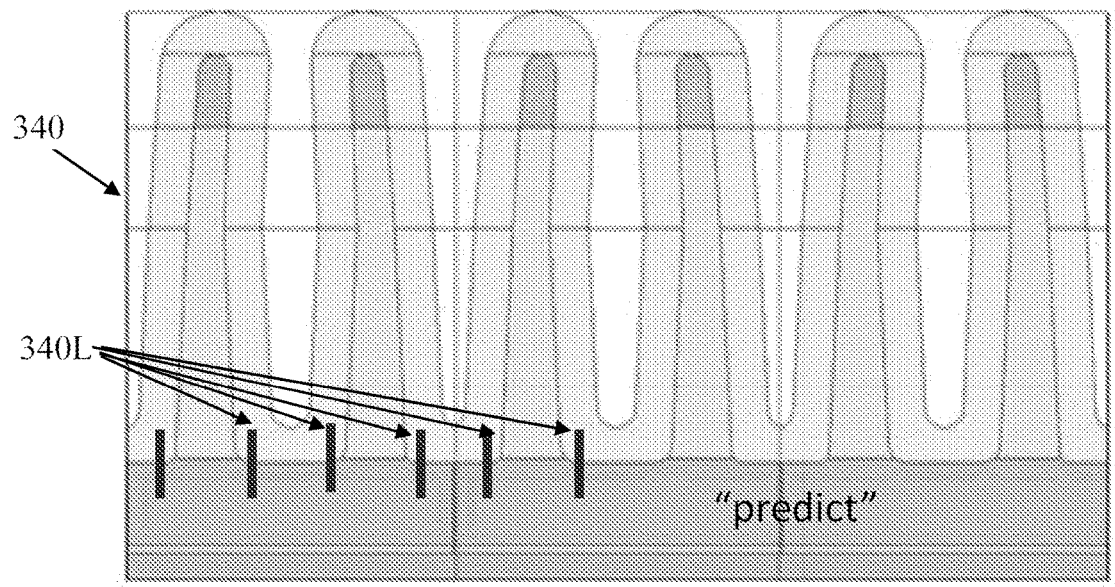
Figure 3E:
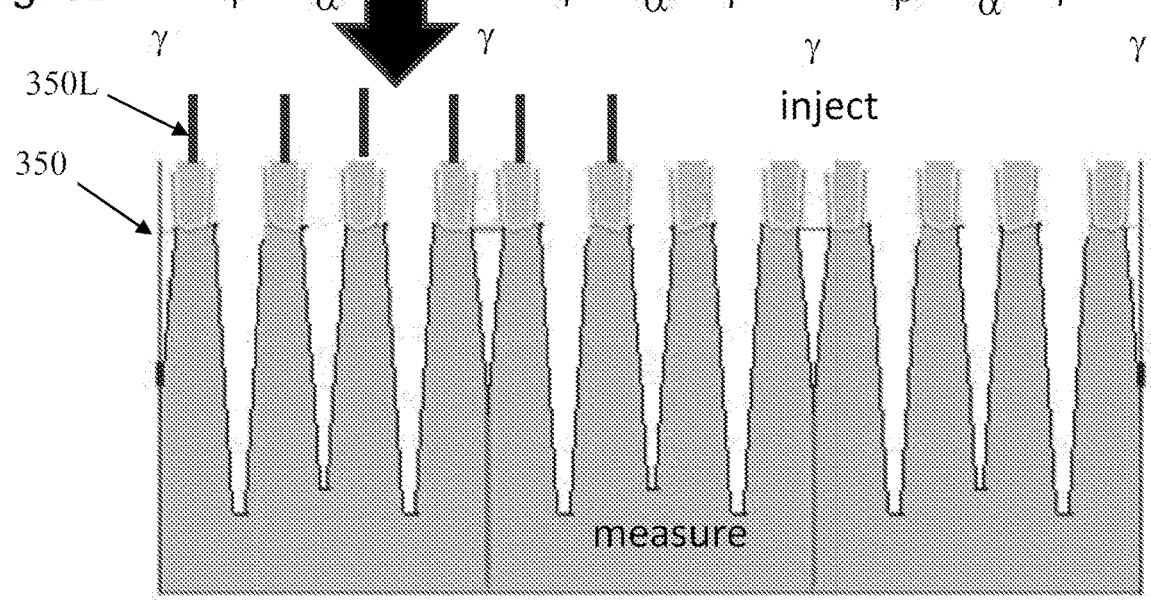

Reference is made to FIG. 1, representing, by way of a block diagram, a system of the invention for use in controlling a multiple patterning process of n patterning stages subsequently applied to a sample to produce a target pattern thereon. The system 100 comprises or is configured as a computerized control unit/system 104 including inter alia such software/hardware utilities/modules as data input (or data readout) utility 104A, data output 104D, memory utility (not shown), and data processor 104B.

As shown in the figure, the control system 100 is associated with an optical measurement unit (constituting a measured data provider) 110. The system 100 may be connectable to data provider 110 (via wires or wireless signal transmission). Such measured data provider 110 may be an optical measurement unit itself which is configured for measuring on the sample being patterned by a patterning tool arrangement 112 (on-line operational mode of system 100) or an external storage device where measured data has been previously stored (off-line operational mode). Considering the on-line mode, the control system 100 may be part of the measurement unit 110, i.e. may be directly connected to a detection system of the measurement unit 110. The construction and operation of the measurement 110 do not form part of the present invention and may utilize any known suitable optical measurement scheme(s) for measuring pattern parameters.

The data input utility 104A receives preliminary or intermediate measured data indicative of the optical response of the sample after being patterned by intermediate m-th patterning stage (m being integer 1≤m<n). This measured data is processed by the processor utility 104B to determine one or more selected parameters of a predetermined pattern feature (in the m-th pattern) enabling to optimize data interpretation model for interpreting optical response of the sample after successive k-th patterning stage m<k≤n).

Thus, the processor utility 104B includes an identification module 106 and a data interpretation module 108. The identification module 106 is adapted for processing intermediate measured data indicative of the optical response of the m-th pattern, and identifying one or more selected parameters of a predetermined pattern feature, and generating data indicative thereof. The interpretation module 108 is adapted for utilizing such parameter(s) in the intermediate pattern and optimizing a data interpretation model, i.e. defining the optimal optical model for interpretation of the optical measured data for the sample being patterned by one or more patterning stage subsequent to the m stages.

Thus, according to the invention predetermined parameter(s) of the intermediate pattern feature is/are used for model optimization. The selected parameter of the m-th pattern feature is that affecting the optical response from the subsequent k-th pattern, irrespective of whether the m-th pattern feature itself exists or not in the k-th pattern. In particular, the inventors have found that such parameter may be associated with the location of a certain feature in the m-th pattern. By optimizing the data interpretation model using this parameter (e.g. fixing this parameter (parameter value) in the model) significantly improves the data interpretation for successive patterning stages to determine weak parameters and adjusting/controlling the patterning process accordingly to reduce pitch walking effect in the target pattern.

In this connection, reference is made to FIG. 2A illustrating an example of a sample being patterned by n patterning stages. Patterning (i.e., photolithography) and etching processes are applied to a sample to form therein trenches noted as α, β and γ. The different (successive) patterning stages are illustrated in which a first core structure (mandrel) noted as Core 1 is first formed on a substrate, then a first spacer noted as Spacer 1 is formed around the first core, and then a second core structure noted as Core 2 as well as a second spacer Spacer 2 are created. These are the main stages of in the Spacer Assisted Double Patterning (SADP) technique. Such techniques utilize the principles of pitch division typically aimed at producing the final pattern with very small and dense features.

It should be noted that the principles of the invention are not limited to this specific patterning technique, i.e. n=2 technique, but can be used for monitoring any multistage patterning process, i.e. n≥2. The entire pattern (target pattern) is thus formed by two or more arrays (sub-patterns) of features created using sequential patterning stages. This typically could result in such undesirable effect as "pitch walking", which should be controlled and eliminated or at least significantly reduced.

FIG. 2B illustrates a SEM picture showing the α, β and γ trenches. These parameters are determined as follows:

Fin≈Spacer2

α≈Spacer1

β≈Core1−2·Spacer2

γ≈Pitch−Core1−2·Spacer1−2·Spacer2

The inventors have found that by monitoring the location of the α, β and γ trenches, pitch walking may be measured and further may be used for process control.

FIG. 2C illustrates different pitch walking parameters α, β and γ with respect to the top core noted as TM, the bottom core noted as BM and the fin structure. In this connection, it should be noted that the pitch parameters is a real measured data, i.e. measurement on real (production) samples is provided. The processing of the real measurements thus does not require prior knowledge of CDs and other structure parameters, and does not require use of any predefined model.

Reference is made to FIGS. 3A-3E illustrating a flow diagram 300 of a method 300 of the present invention for use in controlling a multistage patterning process applied to a sample to create a target pattern. In step 310 and/or 320, preliminary or intermediate measurement session (one or more measurements) could be applied to the sample after an intermediate m-th patterning stage. Considering the example of FIG. 2A where the target pattern is created by a double-stage patterning process, the m-th patterning stage is the first stage. The measurements utilize any known suitable optical measurement technique, for OCD metrology based on the principles scatterometry: measurement of light scattering properties of the sample pattern. Through accurate numerical models, it is then possible to relate the measured scattering properties to the geometrical and material characterizations of the sample pattern.

The measurement technique may be based on measuring the parameters of reflected electromagnetic radiation (intensity, polarization state(s), phase) such as spectral reflectometry (SR), spectral ellipsometry (SE), full Mueller matrix characterization, dome scatterometry, etc. Some examples of the optical suitable to be used in measuring parameters in a patterned structure are described in U.S. Pat. No. 8,531,678 which is assigned to the assignee of the present application, and is incorporated herein by reference. Some measurements may also be not scatterometry measurements, e.g. using TEM tool or CD-SEM tools, etc.

Generally, the measurements could be performed by the same tool (OCD tool), in sequence, by different OCD tools of the same or similar type (e.g. optical). It is possible to use measurements from integrated tools (OCD), installed on corresponding processing equipment (Litho or etch). Measurements also could be performed by tools of different types. The invention is neither limited to any OCD measurement techniques, as well as any specific multiple patterning techniques, such as SADP for example.

In step 320, the intermediate measured data is processed to determine one or more selected parameters of a predetermined feature which affects/predicts a pitch walking parameter in a successive k-th patterning stage (e.g. the second final patterning stage in the double patterning process). More specifically, as shown in FIG. 3B, such selected parameter is the location of a center of a spacer region between two adjacent lines. This selected parameter, which affects a pitch walking parameter in the subsequent k-th pattern is injected into the data interpretation model. Intermediate measured data represented by segments 320L at the bottom of structure of step 320 (indicative of centers of spacers) correspond to the segments 330L at the top of the structure of step 330. These parameters define positions/locations of tops of subsequent step features as illustrated in step 330. Intermediate measurements performed at step 320 provide parameters characterizing locations of a selected feature of the pattern (e.g. centers of spacers). Measurement at step 330 is then performed on the next structure being patterned by k-th subsequent patterning stage and the parameters determined in step 320 (fixed values) correspond to the centers of the tops for step 330. These parameters are injected into a data interpretation model used for interpretation in step 330 of the measurements on the k-th pattern. Position values for centers 330B of features 330Fr are defined. The locations of centers 330L of spacers around these features are represented by lines 340L at the bottom of the structure in step 340. These bottom locations from this step correspond to the tops 350L of final structure of step 350. The values or data on these locations are injected into the data interpretation model for use in the next (final) measurements which enables to define pitch walking related parameter(s) (α, β, γ). Thus, the feature whose parameter(s) is/are selected for measurement at the intermediate patterning stage are actually not present in the patterned sample at said successive step, while the selected parameter(s) affect the parameters of the pattern resulting from the successive step(s), and can therefore be used in the data interpretation model for the successive step data interpretation.

The data interpretation model may include also a "modifier function" accounting for spacer slimming during the etching process.

According to the example of the present invention, the intermediate measured data is used to determine the location e.g. of the center or inner edge of spacers at the bottom of the structure including individual depth of etching for each of the α, β and γ trenches, and such parameters are then transferred to interpret measured data from the subsequent structure. It should be noted that, generally, a smaller number of floating parameters ("floating" parameters of the data interpretation model) may be derived from the intermediate measurement(s), such as CD, SWA, profile, tilt.

Reference is made to FIGS. 4A-4E illustrating an example of controlling the patterning process applied to a sample 400. In this example, the m-th stage after which the intermediate measurement session is applied is the top core etching stage. The parameter (e.g. location) of a predetermined feature (e.g. center of the spacer) of the pattern is determined, and measured data indicative thereof is generated by providing a map of critical dimensions 410. The map of critical dimensions 410 is then used to optimize a dose map 420 and provide an optimized data interpretation model including an optimized dose map and different profile parameters values 430. Thus, the technique of the present invention enables to extract a profile of a structure and "inject" the extracted profile of the structure in the subsequent steps.

FIGS. 4F-4I illustrate the top core spacer deposition stage, in which the profile of the spacer measured in an earlier stage is injected into the data interpretation model and the spacer profile (top, side, bottom) is extracted. The pitch-walking is then could be predicted by measuring the distance from the center of the spacer to the center of the core.

Figure 4F:
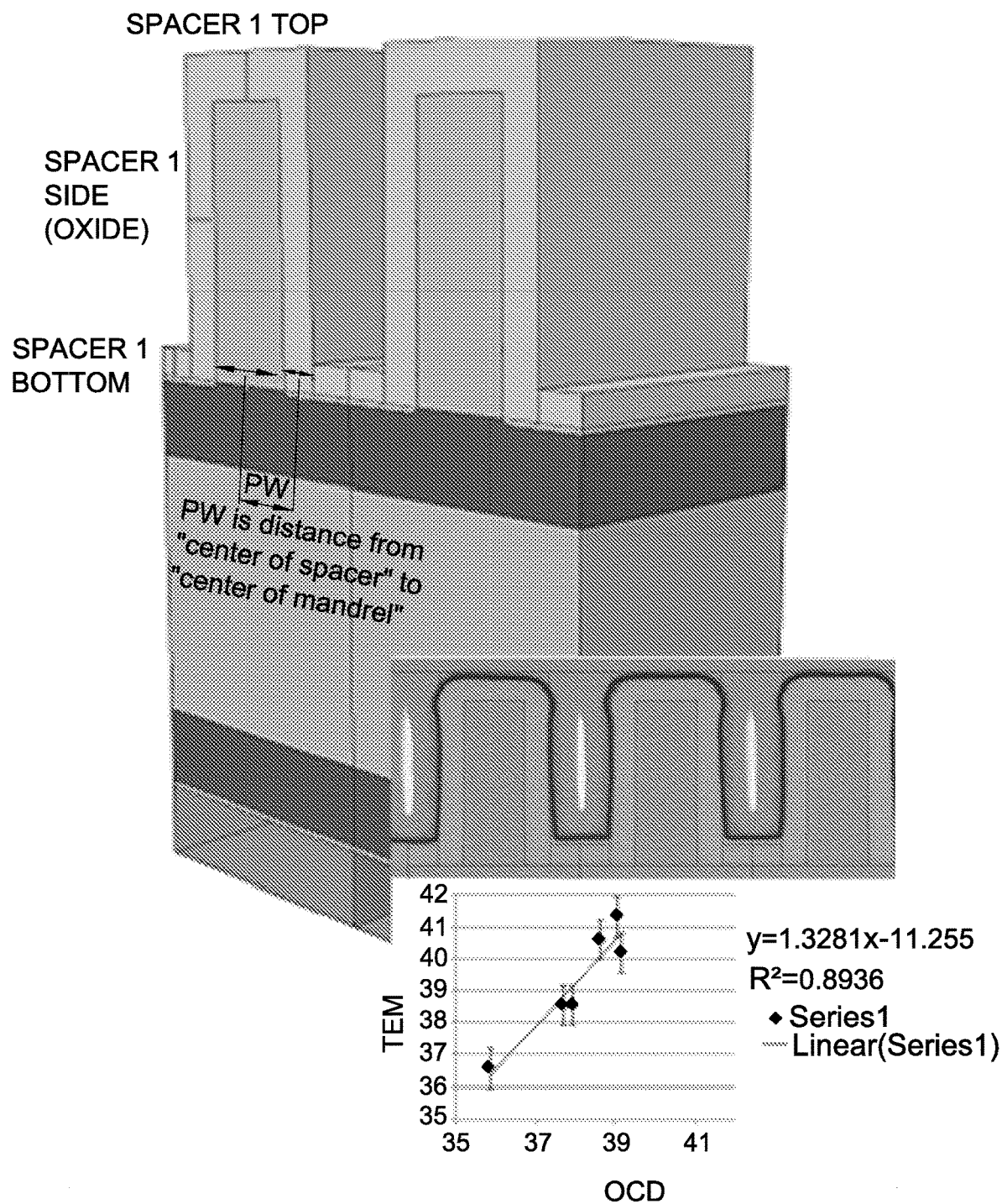
Figure 4I:
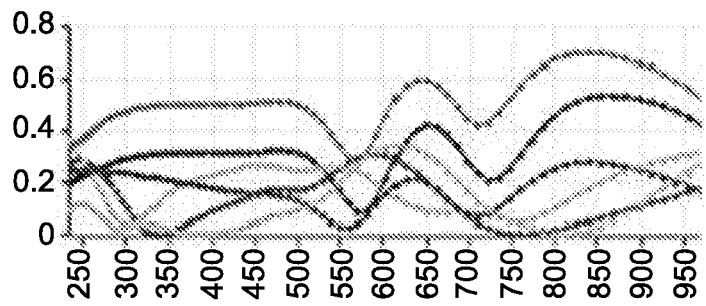
Figure 4J:
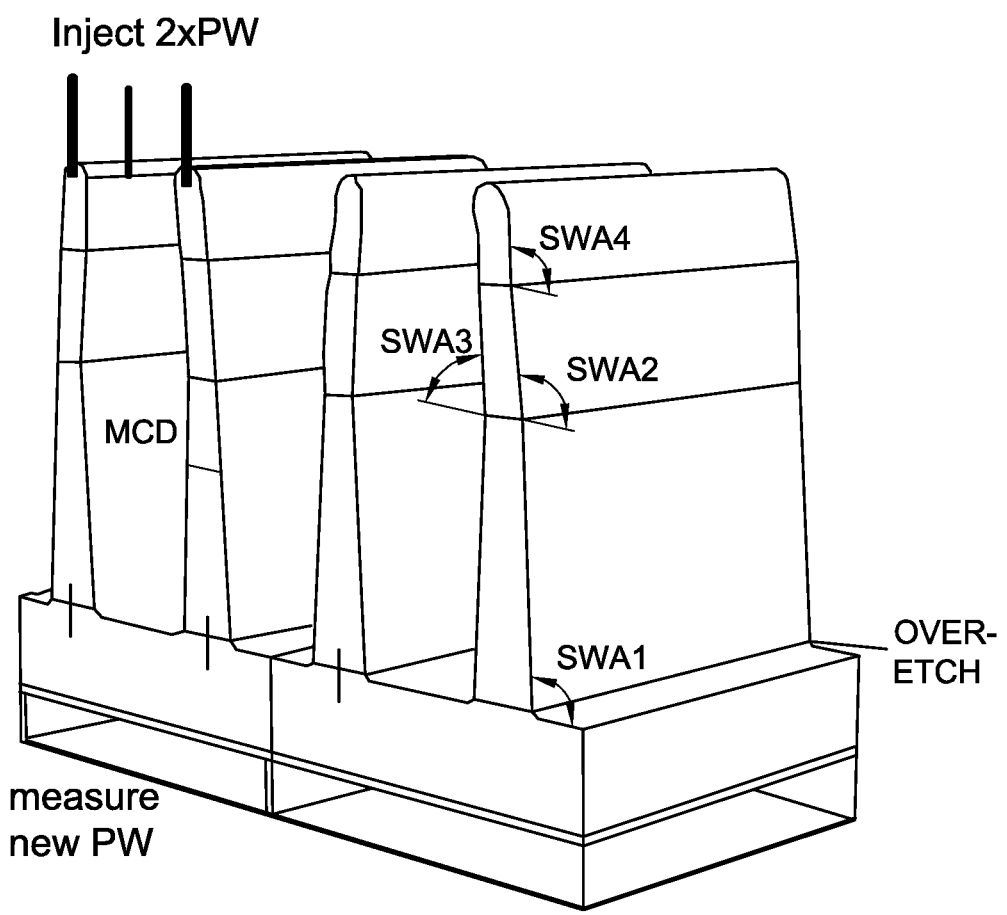
Figure 4K:
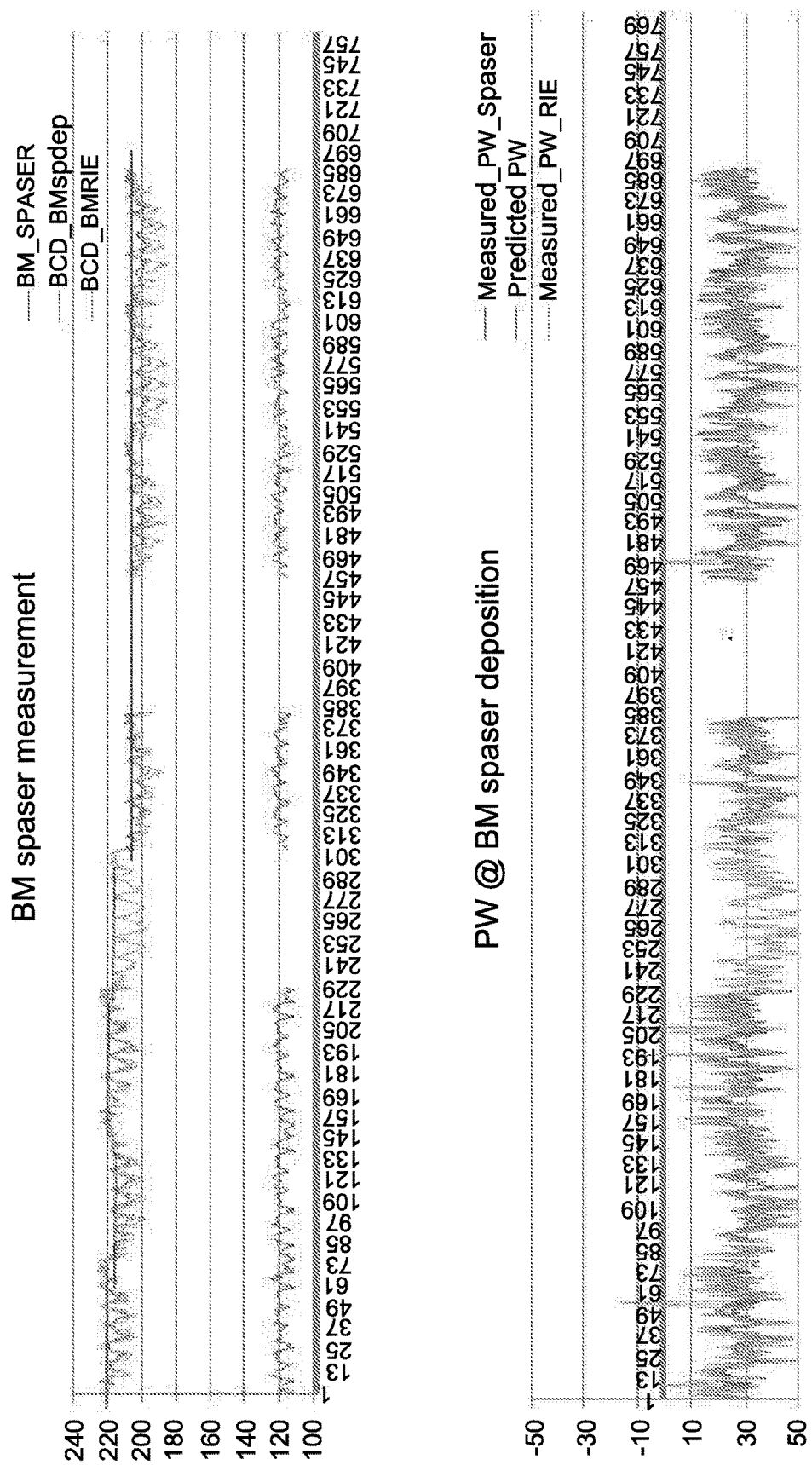

FIGS. 4J and 4K illustrate the bottom core etching and spacer deposition stages, in which the value corresponding to the locations of features' tops extracted from the previous step is used in the subsequent measurements (i.e. injected to the data interpretation model used for interpreting the subsequent measured data). The pitch walking value is then measured based on the measured locations at the bottom of the structure. This step defines the Spacer Self-Aligned Double Patterning (SADP).

The invention claimed is:

1. A method for use in controlling a multiple patterning process including a plurality of patterning stages subsequently applied during a semiconductor manufacturing process to a sample semiconductor wafer to produce a target pattern thereon, wherein the plurality of patterning stages includes a first patterning stage followed by one or more intermediate patterning stages that are followed by a last patterning stage, the method comprising:
monitoring the semiconductor manufacturing process by providing, during any given one of the first or intermediate patterning stages, intermediate measured data indicative of an optical response of the sample, processing said intermediate measured data, determining at least a location parameter of a predetermined feature of the pattern, and generating measured data indicative of said at least one selected parameter, and utilizing said at least location parameter of the predetermined feature to optimize a data interpretation model for interpretation of measured data indicative of an optical response from the sample being patterned by any subsequent intermediate or last patterning stage.

2. The method of claim 1, wherein said at least location parameter of the predetermined feature in the sample after being patterned by the given first or intermediate patterning stage affects one or more parameters of the sample after being patterned by the subsequent intermediate or last patterning stage.

3. The method of claim 2, wherein said predetermined feature is absent in the sample after being patterned by the subsequent intermediate or last patterning stage.

4. The method of claim 1, wherein said processing of the intermediate measured data comprises using a data interpretation model for determining said at least one parameters of the sample.

5. The method of claim 1, wherein said at least location parameter of the predetermined feature is the location of a center of a spacer region between neighboring features of the pattern.

6. The method of claim 1, wherein said multiple patterning process is a Spacer Self-Aligned Double Patterning (SADP) process.

7. The method according to claim 6, wherein said sample after the last patterning stage comprises a core patterned structure and said at least one parameter of the sample includes at least one of α, β and γ values.

8. The method of claim 7, wherein said processing of the measured data comprises calculating at least one of relative or absolute locations of center of spacers defined on both sides of the core patterned structure and relative or absolute locations of inner edges of spacers defined on both sides of the mandrel patterned structure.

9. The method of claim 7, wherein said measuring of at least one pitch walk parameter comprises measuring individual depth of RIE for each of α, β and γ trenches.

10. The method of claim 1, comprising providing a test structure having a periodic patterned structure comprising a series of sets of patterned features; applying a core mask to the test structure to create a first pattern thereon defining the core patterned structure.

11. The method of claim 10, comprising applying optical measurements to the test structure and detecting optical responses of the periodic structure; processing and analyzing data indicative of the detected optical responses to determine a differential optical response and identify the pitch of the pattern.

12. A system for use in controlling a multiple patterning process including a plurality of patterning stages subsequently applied during a semiconductor manufacturing process to a sample semiconductor wafer to produce a target pattern thereon, wherein the plurality of patterning stages includes a first patterning stage followed by one or more intermediate patterning stages that are followed by a last patterning stage, the system comprising:
a control unit comprising data input utility for receiving, during any given one of the first or intermediate patterning stages, a preliminary data indicative of intermediate measured data corresponding to optical response from the sample; and
a processor utility comprising an identification module adapted for processing the intermediate measured data and determining at least a location parameter of a predetermined feature of the pattern, and an interpretation module configured for utilizing said at least location parameter of the predetermined feature to optimize a data interpretation model and defining an optimal optical model for interpretation of measured data indicative of an optical response of the sample after being patterned by any subsequent intermediate or last patterning stage,
wherein the control unit and processor utility are configured to monitor the semiconductor manufacturing process.

13. A measurement system for use in controlling a multiple patterning process including a plurality of patterning stages subsequently applied during a semiconductor manufacturing process to a semiconductor wafer sample to produce a target pattern thereon, the measurement system comprising:
an optical measurement unit configured for detecting optical response of the sample and generating measured data indicative thereof; and the control unit of claim 12 for processing the measured data and determining at least one parameter of the sample, wherein the optical measurement unit and the control unit are configured to monitor the semiconductor manufacturing process.

* * * * *